United States Patent [19]

Macors et al.

[11] Patent Number: 5,086,783
[45] Date of Patent: Feb. 11, 1992

[54] BLOOD SAMPLING DEVICE

[75] Inventors: Paul P. M. G. J. Macors, Liege, Belgium; Henricus F. Paulussen, Eindhoven; Jellard Vos, Hasselt, both of Netherlands

[73] Assignee: Sherwood Medical Company, St. Louis, Mo.

[21] Appl. No.: 607,410

[22] Filed: Oct. 31, 1990

[51] Int. Cl.$^5$ .............................................. A61B 5/00
[52] U.S. Cl. .................................. 128/765; 604/244
[58] Field of Search ............... 128/760, 763, 764, 765; 604/256, 244, 413, 414, 415

[56] References Cited

U.S. PATENT DOCUMENTS

| | | | |
|---|---|---|---|
| 3,900,028 | 8/1975 | McPhee | 604/415 |
| 3,931,815 | 1/1976 | Takatsuki | 128/764 |
| 4,192,320 | 3/1980 | Megahed | 128/764 |
| 4,378,812 | 4/1983 | Sarstedt | 128/765 |
| 4,445,896 | 5/1984 | Gianturco | 604/415 X |
| 4,448,206 | 5/1984 | Martell | 128/765 |
| 4,572,210 | 2/1986 | McKinnon | 128/765 |
| 4,615,341 | 10/1986 | Marzolf et al. | 128/765 |
| 4,673,396 | 7/1987 | Urbaniak | 604/211 |
| 4,774,963 | 10/1988 | Ichikawa et al. | 128/763 |
| 4,856,533 | 8/1989 | Anraku et al. | 128/763 |

Primary Examiner—Max Hindenburg
Attorney, Agent, or Firm—Andrew J. Beck; Montgomery W. Smith; Richard D. Allison

[57] ABSTRACT

A blood sampling kit and the method of using the blood sampling kit are disclosed wherein an arterial blood gas syringe having a venting means associated therewith is used in combination with a blood collection tube holder having a double ended needle mounted therein and a stopper assembly consisting generally of a cylindrical member with a central opening and a flexible diaphragm member extending across the opening such that the stopper assembly and syringe assembly are inserted into the blood collection tube holder to obtain a blood sample from a patient in the syringe assembly and, once the blood sample is obtained, the syringe assembly and stopper assembly are removed from the blood collection tube holder and the stopper assembly protects the blood sample from exposure to the atmosphere.

26 Claims, 3 Drawing Sheets

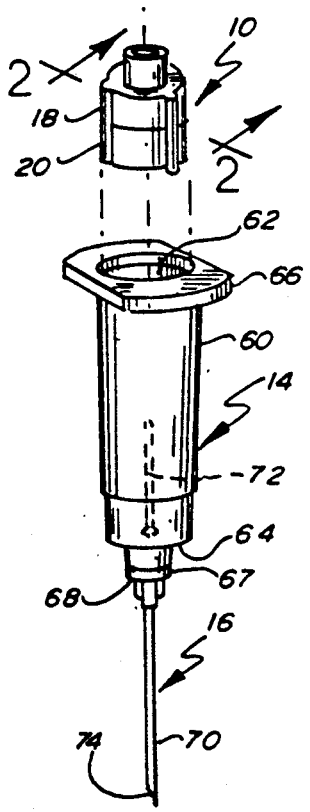
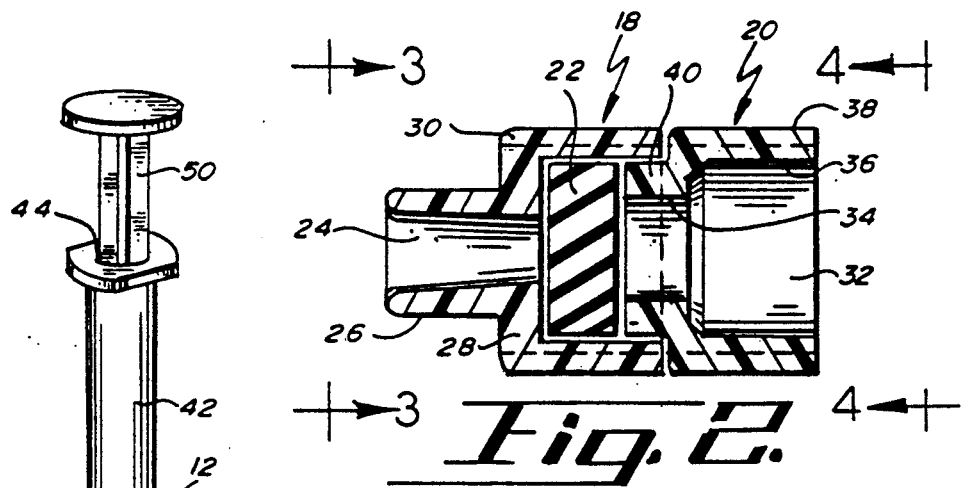
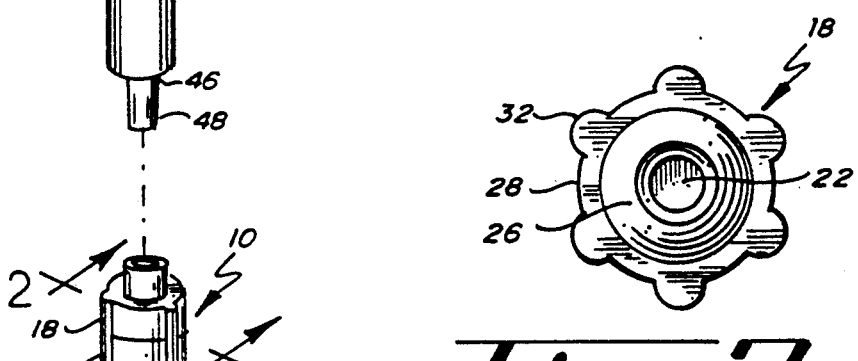
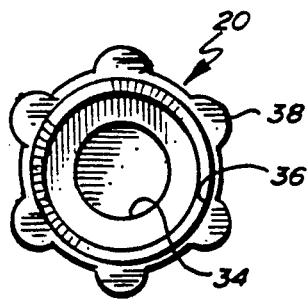

BLOOD SAMPLING DEVICE

FIELD OF THE INVENTION

The present invention relates to a medical device which includes a stopper assembly for use with an arterial blood gas syringe and blood collection tube holder and needle to obtain blood sample from a patient.

BACKGROUND OF THE INVENTION

Blood samples are commonly obtained from a patient using either an arterial blood gas syringe for obtaining arterial blood samples from a patient or by using a vacuum blood collection tube and blood collection tube holder for obtaining venous blood samples from a patient.

In the field of arterial blood gas syringes, numerous designs have been developed in an effort to prevent exposure of a collected blood sample to the atmosphere or to allow for the removal of contaminant gases from the syringe as the blood sample is being drawn. Arterial blood gas syringes typically include a syringe barrel, a standard needle and a plunger rod with a piston member on the distal end thereof. In many of these syringes, the piston member and/or the plunger rod include a venting structure to prevent oxygen or carbon dioxide from reacting with the arterial blood sample so that an accurate measurement of the components of the blood sample may be performed. U.S. Pat. No. 4,615,341 granted to Marzolf et al; U.S. Pat. Nos. 4,373,535 and 4,448,206 granted to Martell and U.S. Pat. No. 4,572,210 granted to McKinnon are illustrative of some of the arterial blood gas syringe designs which include a venting structure associated with the syringe. These devices are designed to allow the physician or nurse to obtain the desired blood sample directly from an artery of the patient by piercing the skin of the patient with the preattached needle.

Another approach to obtaining a blood sample from a patient is illustrated in U.S. Pat. No. 4,192,320 granted to Megahed. The Megahed patent discloses the use of an adaptor for use with a conventional syringe assembly and a conventional blood collection tube holder to obtain a blood sample from the vein of the patient. The adaptor is described as being of a conventional elastomeric, self-sealing material which is frictionally retained on the distal end of the conventional syringe assembly. Once the adaptor has been placed on the distal end of the conventional syringe assembly, this combination is inserted into a blood collection tube holder which has previously been inserted into the vein of the patient. The adaptor and syringe assembly are then inserted into the blood collection tube holder until the proximal end of the double ended needle on the blood collection tube holder pierces the adaptor. The blood sample is then obtained from the vein of the patient by a combination of the patient's venous pressure plus the retraction of the plunger of the syringe assembly to aspirate the blood into the syringe chamber. Once a sufficient venous blood sample has been obtained, the adaptor and syringe assembly are removed from the blood collection tube holder and the collected venous blood sample is then analyzed.

SUMMARY OF THE INVENTION

One object of the present invention is to provide a stopper assembly having a needle piercable diaphragm member therein to prevent exposure of the blood sample to atmospheric air once it has been collected.

Another object of the present invention is to provide a stopper assembly which will assist in aligning the distal end of the syringe with the proximal end of the double ended needle on the blood collection tube holder.

A further object of the present invention is to provide an improved method for obtaining an arterial blood sample from a patient.

As described more fully hereinafter, one form of the present invention includes a stopper assembly which is designed to be frictionally retained on the distal end of an arterial blood gas syringe to enable the assembly to be inserted into a blood collection tube holder. In its preferred form, the stopper assembly consists of a two-piece housing having a diaphragm member centrally positioned therebetween. The preferred arterial blood gas syringe is a commercial product known as the MARZ-175 sold by Sherwood Medical Company, St. Louis, Mo., U.S.A. which is disclosed and more fully described in U.S. Pat. No. 4,615,341 granted to Marzolf et al. The blood collection tube holder consists of an elongate tubular member having an open proximal end with a plurality of finger flanges extending therefrom and a reduced diameter distal end having a double ended needle thereon.

When the nurse or technician desires to obtain an arterial blood sample using the present invention, the distal portion of the double ended needle on the blood collection tube holder is inserted into the artery of the patient. The plunger of the arterial blood gas syringe is then withdrawn to a predetermined position in the syringe barrel to form a sample chamber having the desired volume. The proximal section of the stopper assembly housing is then attached to the tapered distal luer portion of the arterial blood gas syringe. The arterial blood gas syringe and the stopper assembly are then inserted through the proximal end of the blood collection tube holder until the distal section of the stopper assembly housing contacts and compresses a rubber sleeve located on the proximal portion of the double ended needle. The proximal needle point on the double ended needle then pierces the diaphragm member in the stopper assembly. The patient's arterial blood will then flow through the double ended needle and into the sample chamber. As the arterial blood sample flows into the sample chamber, the air in the sample chamber will be forced through the venting structure in the arterial blood gas syringe until only the arterial blood sample remains in the sample chamber. Once the desired blood sample is obtained, the arterial blood gas syringe and the stopper assembly are removed from the blood collection tube holder. The blood sample is then transported to the laboratory where the technician may either remove the stopper assembly from the arterial blood gas syringe or pierce the diaphragm member of the stopper assembly to inject the blood sample into the analyzer.

An advantage of the present invention is that the stopper assembly of the present invention may be used with nearly any syringe or blood collection tube holder.

A further advantage of the present invention is that multiple blood samples may be obtained from the patient or the arterial blood gas syringe may be replaced with a conventional syringe to aspirate the blood sample from the patient without having to repuncture the blood vessel of the patient.

Other objects and advantages of the present invention will become apparent from a review of the following detailed description of the present invention which is intended to more fully describe a preferred form of the present invention.

BRIEF DESCRIPTION OF THE DRAWINGS

FIG. 1 is an exploded perspective view of the arterial blood gas syringe, stopper assembly and blood collection tube holder and needle of the present invention;

FIG. 2 is a cross-sectioned view of the stopper assembly of the present invention taken generally along lines 2—2 of FIG. 1;

FIG. 3 is a top view of the stopper assembly of the present invention;

FIG. 4 is a bottom view of the stopper assembly of the present invention;

DETAILED DESCRIPTION OF THE PREFERRED EMBODIMENT

Figure 5:
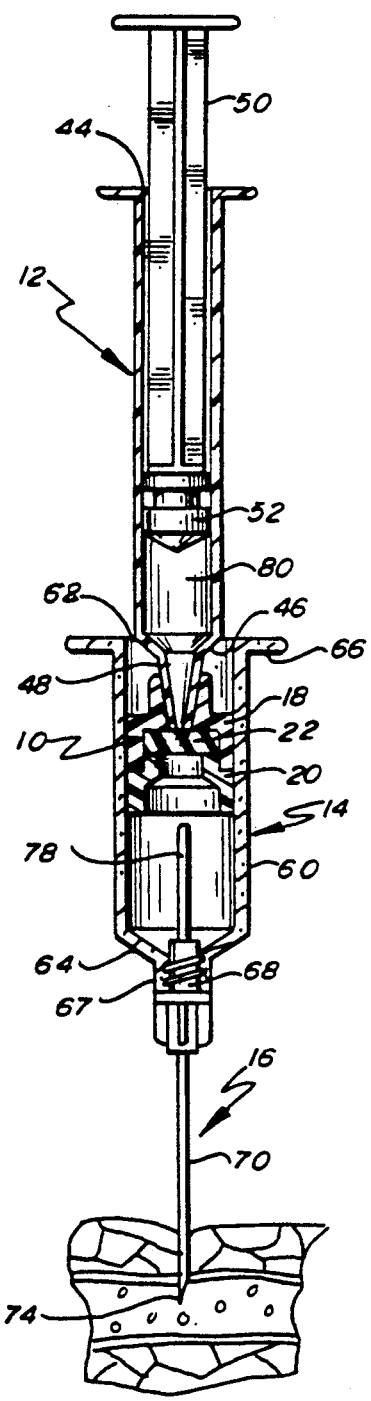
FIG. 5 is a partially cross-sectioned plan view showing the blood collection tube holder and needle of the present invention with the arterial blood gas syringe and stopper assembly partially inserted therein.

The present invention consists generally of a stopper assembly 10, an arterial blood gas syringe 12 and a blood collection tube holder 14 and needle 16. As described herein, the distal end of a part is the end of the part designed to be positioned closest to the patient. The proximal end of a part is the end of the part designed to be positioned away from the patient.

As shown in FIGS. 2-4, the stopper assembly 10 of the present invention includes a proximal housing section 18 and a distal housing section 20, both of which are preferably constructed of a semi-rigid plastic such as polypropylene. The proximal housing section 18 and the distal housing section 20 are preferably ultrasonically welded or otherwise bonded together to retain an air impervious and needle piercable diaphragm member 22 therebetween. As shown in the drawings, the diaphragm member 22 is a generally circularly-shaped member which is preferably constructed of flexible material such as latex.

As shown in FIGS. 2 and 3, the generally cylindrical proximal housing section 18 includes a central opening 24 extending lengthwise therethrough. The proximal portion of the proximal housing section 18 includes a first section 26 with the preferred inner diameter of the central opening 24 being approximately 4.5 mm and with an inward taper of approximately 6°. The preferred outer diameter of the first section 26 is approximately 6.8 mm and extends proximally approximately 6.8 mm from the distally positioned second section 28. As shown in FIG. 2, the second section 28 of the proximal housing section 18 includes a plurality of evenly spaced and longitudinally aligned positioning ribs 30 extending radially outwardly from the circumference of the second section 28. The preferred outer diameter of the second section 28 is approximately 11.8 mm as measured from the outer surface of the positioning ribs 30. The diameter of the central opening 24 in the second section 28 is sized to receive a portion of the distal housing section 20 therein and has a preferred diameter of approximately 7.5 mm. The preferred length of the proximal housing section 18 is approximately 12 mm and the preferred length of the assembled stopper assembly 10 is approximately 19 mm.

As shown in FIGS. 2 and 4, the generally cylindrical distal housing section 20 includes a central opening 32 extending therethrough. The central opening 32 of the distal housing section 20 preferably includes a proximal section 34 having a preferred inner diameter of approximately 4.5 mm and a distal section 36 having a preferred inner diameter of approximately 7.5 mm. As an alternative to the use of the central opening 32 having inner diameters for the proximal section 34 and the distal section 36, it is anticipated that the central opening 32 may be tapered inwardly or chamfered to facilitate locating the needle 16 in the distal end of the arterial blood gas syringe 12. The outer surface of the distal housing section 20 preferably includes a plurality of equally spaced and longitudinally extending positioning ribs 38 which extend radially outwardly and proximally from the distal end of the distal housing section 20 approximately 7 mm so that the preferred outer diameter of the distal housing section 20 is approximately 11.8 mm as measured along the positioning ribs 38. The proximal end of the distal housing section 20 includes a proximally extending lip 40 which extends approximately 1.3 mm from proximal side of the distal housing section 20 and is sized to be received in the distal portion of the second section 28 of the proximal housing section 18 to allow the distal housing section 20 and the proximal housing section 18 to be ultrasonically welded or otherwise bonded together.

As described briefly above, a diaphragm member 22 is fixedly retained in the stopper assembly 10 by the distal housing section 20 and the proximal housing section 18. As shown in FIG. 2, the lip 40 on the distal housing section 20 extends into the second section 28 a sufficient distance to retain the diaphragm member 22 therein when the distal housing section 20 and the proximal housing section 18 are ultrasonically welded or otherwise assembled to form a unitary stopper assembly 10 wherein the diaphragm member 22 separates the central opening 24 of the proximal housing section 18 and the central opening 32 of the distal housing section 20.

Figure 8:
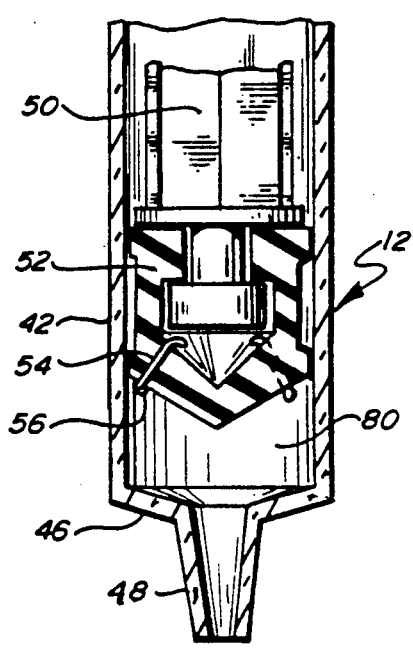
FIG. 8 is a partial cross-sectional view of the distal portion of the preferred form of the arterial blood gas syringe shown in FIG. 1.
Figure 9:
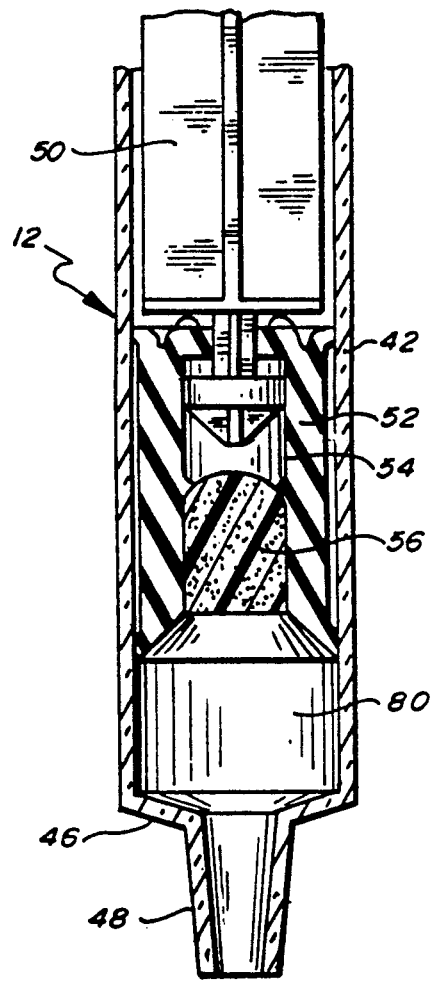
FIG. 9 is a partial cross-sectional view of the distal portion of an alternate form of an arterial blood gas syringe which may be used with the stopper assembly of the present invention.

As shown in FIGS. 1, 8 and 9, the stopper assembly 10 of the present invention is preferably designed for use with an arterial blood gas syringe 12 although it is anticipated that in certain situations as described hereinafter, a conventional syringe assembly may also be used with the present invention.

In describing the preferred forms of the arterial blood gas syringe 12 as shown in FIGS. 1, 8 and 9, like numbers have been applied to like elements. The preferred form of the arterial blood gas syringe 12 used with the present invention has a capacity of approximately 3 cc and a preferred outer diameter of approximately 11 mm.

As shown in the drawings, the arterial blood gas syringe 12 consists generally of an elongate and tubular barrel section 42 having an open proximal end 44 and a reduced diameter distal end 46 with a gradually tapering luer extension 48 extending therefrom. An elongate plunger rod 50 extends distally into the open proximal end 44 of the barrel section 42. The distal end of the plunger rod 50 preferably includes an elastomeric piston 52 thereon which sealingly contacts the inner surface of the barrel section 42. As shown in FIGS. 8 and 9, the piston 52 preferably includes at least one air passageway 54 extending therethrough. The air passageway 54 preferably includes a venting member 56 such as a porous thread (FIG. 8) or a porous plug member (FIG. 9) extending therethrough, the function of which are described more fully hereinafter. Additionally, the inner surface of the distal end of the barrel section 42 will typically include an anticoagulant such as heparin therein to limit or prevent the clotting of the blood sample as described hereinafter.

Figure 6:
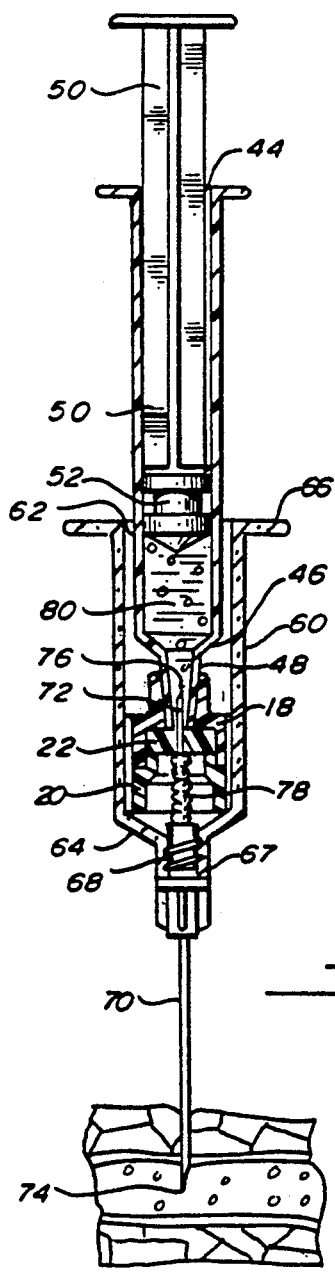
FIG. 6 is a partially cross-sectioned plan view showing the blood collection tube holder and needle of the present invention with the syringe and stopper assembly inserted therein to receive a blood sample in the sample chamber of the arterial blood gas syringe.

As shown in FIGS. 1, 5 and 6, the blood collection tube holder 14 consists generally of an elongate and cylindrically-shaped barrel section 60 which has a slight inward taper from the open proximal end 62 to the substantially closed distal end 64. The proximal end 62 preferably includes a plurality of radially and outwardly extending finger members 66 and the distal end 64 of the blood collection tube holder 14 preferably includes an internally threaded distal extension 67 which is designed to removably receive the threaded hub 68 of the double ended needle 16 therein. The double ended needle 16 is generally linear and includes distal and proximal needle sections, 70 and 72 respectively, which further include distal and proximal needle points thereon, 74 and 76, respectively. As shown in the drawings, the proximal needle section 72 and the proximal needle point 76 are encircled by a resilient rubber sleeve member 78 which encloses the proximal needle section 72 and proximal needle point 76 prior to and after use of the present invention as described more fully hereinafter.

Assembly and use of the present invention is relatively simple and provides a convenient way to obtain one or more blood samples from a single puncture in the artery or blood vessel of a patient. When the nurse or technician desires to obtain a blood sample from the patient, the needle 16 is threadedly attached to the blood collection tube holder 14 and the plunger rod 50 of the arterial blood gas syringe 12 is withdrawn to move the piston 52 proximally in the barrel section 42 of the arterial blood gas syringe 12 to form a sample chamber 80 having the desired sample volume between the piston 52 and the distal end 46 of the barrel section 42. The stopper assembly is then frictionally, threadedly or otherwise attached to the luer extension 48 of the arterial blood gas syringe 12 by inserting the luer extension 48 into the central opening 24 of the proximal housing section 18 so that the luer extension 48 is retained in the first section 26 of the proximal housing section 18.

Once this preliminary assembly of the present invention has been completed, the nurse or technician may insert the distal needle section 70 of the needle 16 into the patient so that the distal needle point 74 extends into the artery of the patient. When the needle 16 has been inserted into the artery of the patient, the sleeve member 78 on the proximal needle section 72 prevents the flow of blood through the needle 16 until the sleeve member 78 is compressed as described hereinafter.

Next, the nurse or technician inserts the stopper assembly 10 and arterial blood gas syringe 12 combination into the proximal end 62 of the blood collection tube holder 14. Because the outer circumference of the stopper assembly 10, as measured around the positioning ribs, 30 and 38, is only slightly smaller than the inner circumference of the blood collection tube holder 14 and is larger than the outer circumference of the arterial blood gas syringe 12, the alignment of the proximal needle section 72 with the central openings 32 and 24 of the stopper assembly 10 is ensured as the stopper assembly 10 is moved distally in the blood collection tube holder 14. The relative size of the stopper assembly 10 with respect to the inner circumference of the blood collection tube holder 14 ensures that the proximal needle section 72 of the needle will be aligned to pierce the diaphragm member 22 and enter a portion of the luer extension 48 as the stopper assembly 10 and arterial blood gas syringe 12 are inserted distally into the blood collection tube holder 14. The use of the positioning ribs, 30 and 38, on the stopper assembly 10 allows any air that is displaced in the blood collection tube holder 14 to flow around the sides of the stopper assembly and out of the proximal end 62 of the blood collection tube holder 14. Additionally, by constructing the distal housing section 20 of the stopper assembly 10 of a semi-rigid material, if the proximal needle section 72 is somehow misaligned with the central opening 32, the proximal needle section will be deflected to realign the needle 16 with the diaphragm member 22 in the stopper assembly 10 and the luer extension 48 of the arterial blood gas syringe 12.

As the stopper assembly 10 and arterial blood gas syringe 12 reach the distal end 64 of the blood collection tube holder 14, the sleeve member 78 will contact the diaphragm member 22. Initially, the proximal needle point 76 will pierce the sleeve member 78. Next, as the stopper assembly 10 and arterial blood gas syringe 12 are moved further distally in the blood collection tube holder 14, the sleeve member 78 will become compressed to expose the proximal needle point 76 and the proximal needle point 76 will pierce the diaphragm member 22 and enter a portion of the luer extension 48. The overall length of the stopper assembly 10 is chosen so that even if the piston 52 of the arterial blood gas syringe 12 is positioned at the distal end 46 of the barrel section 42, the proximal needle point 76 will not pierce the piston 52.

Once the proximal needle point 76 pierces the sleeve member 78 and the diaphragm member 22, the arterial pressure of the patient will force the blood sample into the sample chamber 80, the air which is displaced from the sample chamber 80 will flow through the air passageway 54 and venting member 56 in the piston 52 as shown in FIG. 6. Alternately, it is anticipated that the arterial blood gas syringe 12 may include a variety of other venting mechanisms such as a mechanical venting mechanism allow the air to pass therethrough and to seal the sample chamber 80 once the blood sample has been obtained. As all of the air is forced out of the sample chamber 80, the blood sample will wet the venting member 56 which automatically swells or otherwise closes the air passageway 54 in the piston 52.

Figure 7:
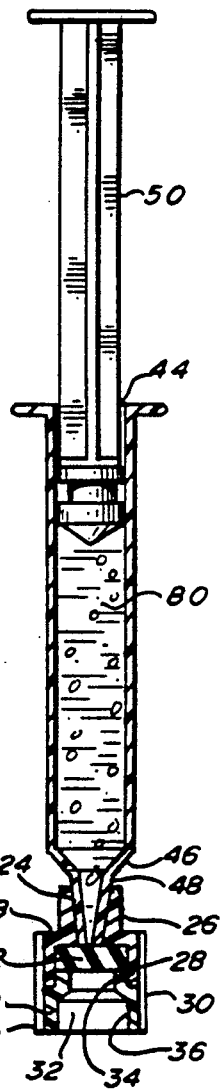
FIG. 7 is a partially cross-sectioned plan view showing the arterial blood gas syringe and stopper assembly of the present invention having a collected blood sample therein.

Once the sample chamber 80 is filled and the air passageway 54 is closed, the arterial blood gas syringe 12 and the stopper assembly 10 may be withdrawn from the blood collection tube holder 14 as shown in FIG. 7. As the proximal needle point 76 is withdrawn from the stopper assembly 10, the diaphragm member 22 will close and form an air-tight seal with the distal end 46 of the arterial blood gas syringe 12 and the sleeve member 78 will return to its original position to prevent the flow of blood through the needle 16. If another blood sample is desired, the foregoing steps may be repeated without the need to repuncture the artery of the patient.

If there is insufficient arterial blood pressure to sufficiently fill the sample chamber 80, such as when the patient is in shock, the arterial blood gas syringe 12 and the stopper assembly 10 may b quickly removed from the blood collection tube holder 14 and the arterial blood gas syringe 12 may be replaced with a conventional syringe assembly (not shown). In this situation, the piston will be positioned at the distal end of the syringe assembly as the stopper assembly 10 is placed on the luer extension. Once the stopper assembly 10 and the syringe assembly are inserted into the blood collection tube holder 14 as described above, the blood sample may be obtained by withdrawing the plunger rod and piston of the syringe assembly to aspirate the blood sample into the syringe assembly. When the blood sample has been obtained and the stopper assembly 10 and syringe assembly are withdrawn from the blood collection tube holder 14, the diaphragm member 22 in the stopper assembly 10 will form an air tight seal with the distal end of the syringe assembly and the sleeve member 78 will return to its original position along the proximal needle section 72 to prevent the flow of blood through the needle 16.

As shown in FIGS. 1, 5 and 6, the stopper assembly 10 of the present invention is preferably used with a blood collection tube holder 14 having a double ended needle 16 which is preferably removably mounted thereon. As set forth herein, the relative preferred dimensions for the blood collection tube holder 14 are for a blood collection tube holder known in the medical industry as a pediatric blood collection tube holder. The pediatric blood collection tube holder has in inner diameter of approximately 12 mm and is designed to receive a blood collection tube having a diameter of approximately 10.25 mm therein. It should be understood that the preferred dimensions for the stopper assembly 10 as set forth herein are for use with a pediatric sized blood collection tube holder. When the stopper assembly 10 of the present invention is used with a blood collection tube holder known in the medical industry as an adult blood collection tube holder, the relative dimensions of the stopper assembly will likewise be proportionately increased so that the stopper assembly may be used with adult blood collection tube holders which are designed to receive blood collection tubes having a diameter of either 13 mm or 16 mm therein while retaining the preferred relative dimensions of the present invention wherein the outer diameter of the syringe assembly is preferably smaller than the diameter of the stopper assembly and the outer diameter of the stopper assembly is preferably smaller than the inner diameter of the blood collection tube holder.

What is claimed is:

1. A blood sampling kit for obtaining a blood sample from a patient, said kit comprising:
   a syringe assembly having first outer diameter, an elongate barrel section with a reduced diameter distal end and a piston member movably positioned in said barrel section to form a sample chamber between said distal end of said barrel section and said piston member;
   a stopper assembly having distal and proximal ends and a second outer diameter, said stopper assembly further including a needle piercable diaphragm member operatively associated therewith;
   an elongate and generally cylindrical blood collection tube holder having distal and proximal ends and an inner diameter, said blood collection tube holder further including a needle with distal and proximal needle points thereon wherein said needle is operatively associated with said distal end of said blood collection tube holder; and
   said stopper assembly is sized to be completely received in said blood collection tube holder and said second outer diameter of said stopper assembly is intermediate said first outer diameter of said syringe assembly and said inner diameter of said blood collection tube holder.

2. The blood sampling kit of claim 1 wherein said syringe assembly includes a means for venting said sample chamber operatively associated therewith to allow for the removal of air from said sample chamber while preventing the flow of the blood sample from the patient therethrough.

3. The blood sampling kit of claim 2 wherein said means for venting said sample chamber includes a filter member operatively associated with said piston member.

4. The blood sampling kit of claim 1 wherein said syringe assembly includes a plunger rod operatively associated with said piston member to allow for the manual adjustment of the size of said sample chamber.

5. The blood sampling kit of claim 1 wherein said stopper assembly includes a distal opening extending from said distal end thereof to receive said proximal needle point therethrough and wherein said proximal needle point is adapted to pierce said diaphragm member and is prevented from contacting said piston member of said syringe by contact between said distal end of said stopper assembly and said distal end of said inner diameter of said blood collection tube holder.

6. The blood sampling kit of claim 1 wherein said syringe assembly includes a luer extension extending distally from the distal end of said barrel section and said stopper assembly includes a proximal opening extending inwardly from said proximal end of said stopper assembly and wherein said proximal opening is adapted to receive said luer extension therein such that said diaphragm member is positioned distally of said luer extension.

7. The blood sampling kit of claim 1 wherein said stopper assembly includes a distal opening extending inwardly from said distal end thereof and a proximal opening extending inwardly from said proximal end thereof and wherein said diaphragm member is operatively positioned therebetween.

8. The blood sampling kit of claim 7 wherein said distal opening of said stopper assembly is larger than said proximal opening and said proximal section of said needle includes a proximal needle point thereon which is adapted to extend through said distal opening and said diaphragm member into said proximal opening of said stopper assembly and said distal opening is sized to receive a sleeve member on said proximal section of said needle therein.

9. The blood sampling kit of claim 1 wherein said stopper assembly is constructed of a first material with a central opening extending therethrough and said diaphragm member extends thereacross and is constructed of a second material which is more flexible than said first material.

10. A stopper assembly for use with a syringe and a blood collection tube holder having a needle associated therewith to obtain a blood sampling from a patient, said stopper assembly comprising:
   a housing assembly having distal and proximal ends and an outer circumference sized to be fully received in a blood collection tube holder, said housing assembly being constructed of a first material and including a central opening extending generally therethrough;
   a flexible diaphragm member positioned across said central opening and constructed of a second material which is more flexible than said first material and said diaphragm member is positioned across said central opening such that a distal opening is formed adjacent to said distal end that is larger than a proximal opening formed adjacent said proximal end.

11. The stopper assembly of claim 10 further including a plurality of rib members extending outwardly from said outer circumference of said housing assembly to assist in aligning said distal opening with a portion of the needle on the blood collection tube holder.

12. The stopper assembly of claim 10 wherein said housing assembly includes distal and proximal housing sections both of which have a central opening extending therethrough and wherein said diaphragm member is fixedly retained between said distal and proximal housing sections.

13. The stopper assembly of claim 12 wherein said central opening in said proximal housing section has a first diameter and said central opening in said distal housing section has a second diameter wherein said second diameter is larger than said first diameter and said diaphragm member is positioned between said central opening on said distal housing section and said central opening on said proximal housing section.

14. A blood sampling kit comprising:
   a syringe assembly having a first diameter and a generally tubular barrel section with an open proximal end and a reduced diameter distal end, a plunger rod and a piston member adapted to be movable in said barrel section to form a sample chamber between said piston member and said distal end of said barrel section;
   a venting means operatively associated with said syringe assembly wherein said venting means is adapted to vent air from said sample chamber while retaining a collected blood sample therein;
   a stopper assembly having a second diameter and distal and proximal ends, said stopper assembly including a housing section with a generally centrally located opening extending therethrough and a flexible diaphragm member wherein said diaphragm member is oriented to extend across said opening to form a distal opening distally thereof and a proximal opening proximally thereof;
   a blood collection tube holder having a first inner diameter and an open proximal end adapted to receive said stopper assembly and said syringe assembly therethrough and a reduced diameter distal end with a needle associated therewith wherein said needle includes distal and proximal sections thereon and a hub means for operatively mounting said needle on said blood collection tube holder; and
   wherein said second diameter of said stopper assembly is smaller than said inner diameter of said blood collection tube holder such that said stopper assembly is fully received therein and said distal end of said stopper assembly operatively contacts said reduced diameter distal end of said blood collection tube holder and wherein said proximal needle section extends through said distal opening and said diaphragm member in said stopper assembly to communicate with said sample chamber.

15. The blood sampling kit of claim 14 wherein said opening in said stopper assembly includes said distal opening and said proximal opening separated by said diaphragm member and said proximal opening is sized to receive a portion of said syringe assembly therein and wherein said distal opening is sized to receive a sleeve member on said proximal needle section and a portion of said proximal needle section therein.

16. The blood sampling kit of claim 14 wherein said first diameter of said syringe assembly is smaller than said second diameter of said stopper assembly.

17. The blood sampling kit of claim 14 wherein said stopper assembly includes a plurality of radially extending rib members thereon to assist in aligning the opening in the stopper assembly with the proximal needle section.

18. A method for obtaining a blood sample from a patient including the steps of
   positioning a piston member in the elongate barrel section of a first syringe assembly having an open proximal end and a reduced diameter distal end to form a sample chamber between the piston member and the distal end of the barrel section;
   placing a stopper assembly on the distal end of the first syringe assembly wherein the stopper assembly includes a generally cylindrical housing section and a flexible diaphragm member associated therewith;
   inserting the distal end of a needle having proximal and distal ends into a blood vessel of a patient wherein the needle is operatively associate with a blood collection tube holder having an open proximal end;
   inserting the first syringe assembly and stopper assembly combination into the open proximal end of a blood collection tube holder having a needle with distal and proximal ends thereon and wherein the distal end of the needle has previously been inserted into a blood vessel in a patient and containing insertion of the combination into the blood collection tube holder until the proximal end of the needle passes through the diaphragm member of the stopper assembly and into the distal end of the syringe assembly; and
   collecting a blood sample from a patient in the sample chamber of the first syringe assembly.

19. The method of claim 18 wherein as the blood sample is collected in the sample chamber of the first syringe assembly, air is allowed to pass from the sample chamber to the atmosphere through a venting means associated with the first syringe assembly.

20. The method of claim 18 wherein the first syringe assembly is replaced with a second syringe assembly having a piston member positioned adjacent to the distal end of the barrel section and the piston member in the barrel section to is withdrawn aspirate a blood sample from the patient into the second syringe assembly.

21. A stopper assembly and blood collection tube holder for use in a blood sampling kit, said stopper assembly and tube holder comprising:
- an elongate tubular member having an open proximal end and a reduced diameter distal end,
- a housing assembly having an outer circumference, distal and proximal ends and an opening extending generally therethrough between said distal and proximal ends said housing assembly being sized to be fully received in said tubular member,
- a flexible diaphragm member fixedly attached to said housing assembly and extending across said opening in said housing assembly such that the distance between said distal end of said housing assembly and said diaphragm member is greater than the distance between said proximal end of said housing assembly and said diaphragm member.

22. The medical device of claim 21 wherein said housing assembly is constructed of a first material and said diaphragm member is constructed of a second material and wherein said second material is less rigid than said first material.

23. The medical device of claim 21 wherein said outer circumference of said housing assembly includes a plurality of positioning members thereon to operatively contact said tubular member when said housing assembly is inserted therein.

24. A blood sampling kit comprising:
- a syringe assembly including an elongate barrel section having an open proximal end and a reduced diameter distal end and a piston member having distal and proximal ends and said piston member is adapted to be movably positioned in said barrel section,
- means for venting air operatively associated with said syringe assembly to allow air to selectively flow between said distal end of said piston member and said proximal end of said barrel section,
- a stopper assembly including a needle piercable diaphragm member operatively associated therewith, said stopper assembly including a distal opening thereon and a proximal end adapted to be operatively associated with said distal end of said barrel section,
- an elongate and generally cylindrical member having an open proximal end and a reduced diameter distal end wherein said stopper assembly and said distal end of said barrel section are adapted to be fully received therein, and
- an elongate needle means operatively associated with said distal end of said cylindrical member, said needle means including a proximal needle point thereon to pierce said diaphragm member and includes a sleeve member thereon which is received in said distal opening of said stopper assembly.

25. The blood sampling kit of claim 24 wherein said stopper assembly includes a distal end surrounding said distal opening and said distal end operatively contacts said distal end of said cylindrical member to prevent said proximal needle point from contacting said distal end of said piston member.

26. A blood sampling kit comprising:
- a syringe assembly including an elongate barrel section having an inner diameter, an open proximal end and a reduced diameter distal end and a plunger member including a piston member thereon, said piston member including distal and proximal ends thereon and said piston member is operatively movable in said barrel section between said distal and proximal ends of said barrel section,
- means for venting on said piston member to allow air to selectively flow between said distal end of said plunger member and said proximal end of said barrel section,
- a stopper assembly including an outer diameter, distal and proximal ends thereon and a diaphragm member operatively associated therewith to form a distal opening between said distal end and said diaphragm member and a proximal opening between said proximal end and said diaphragm wherein said proximal opening between said proximal end and said diaphragm wherein said proximal opening is smaller than said distal opening and said proximal opening is sized to receive a portion of said syringe assembly therein,
- an elongate and generally cylindrical member having an inner diameter sized to receive the entire stopper assembly therein, an open proximal end and a reduced diameter distal end,
- an elongate needle member having distal and proximal needle sections with a hub means therebetween wherein said hub means is operatively associated with said distal end of said cylindrical member such that said distal needle section extends distally thereof and said proximal needle section extends into said inner diameter of said cylindrical member, said proximal needle section including a sleeve member thereon, and
- wherein said stopper assembly is sized such that said distal end of said stopper assembly operatively contacts said distal end of said cylindrical member along said inner diameter thereof, said sleeve member is received in said distal opening of said stopper assembly and said proximal needle section extends through said distal opening and diaphragm member to a position distally of said distal end of said piston member.

* * * * *